United States Patent [19]
Whitehead et al.

[11] 4,315,507
[45] Feb. 16, 1982

[54] SANITARY NAPKIN WITH HEAT FUSIBLE BAFFLE

[75] Inventors: Howard A. Whitehead; Attila Matray, both of Appleton, Wis.

[73] Assignee: Kimberly-Clark Corporation, Neenah, Wis.

[21] Appl. No.: 139,580

[22] Filed: Apr. 11, 1980

[51] Int. Cl.³ .............................................. A61F 13/16
[52] U.S. Cl. ................................ 128/287; 128/290 R; 428/288; 428/297; 156/201
[58] Field of Search .............. 128/287, 290 W, 290 R; 428/288, 297, 409, 516; 156/201

[56] References Cited

U.S. PATENT DOCUMENTS

| | | | |
|---|---|---|---|
| 3,294,091 | 12/1966 | Morse | 128/290 R |
| 3,612,054 | 10/1971 | Matsuda et al. | 128/287 |
| 3,665,922 | 5/1972 | Skora | 128/290 W |
| 3,683,917 | 8/1972 | Comerford | 128/287 |
| 3,843,478 | 10/1974 | Zuscik | 128/290 W |
| 3,965,906 | 6/1976 | Karami | 128/287 |
| 4,100,324 | 7/1978 | Anderson et al. | 428/297 |
| 4,200,103 | 4/1980 | Black et al. | 128/290 W |

FOREIGN PATENT DOCUMENTS 648141 12/1950 United Kingdom ............ 128/290 R

Primary Examiner—P. Ives
Attorney, Agent, or Firm—Howard Olevsky; William D. Herrick

[57] ABSTRACT

A sanitary device, e.g. a sanitary napkin is provided which has an absorbent matrix and a fluid impervious baffle. Part of the fluid impervious baffle is a heat fusible sheet which is adhered to the absorbent component by fusing. The absorbent component may have heat fusible material interspersed therein and may have a fluid pervious upper layer which is essentially coterminous with or wraps about the absorbent component or the absorbent component and baffle combination. When a fluid pervious wrap is used, it is preferred that the wrap be fusible and also be fused to the baffle. The fusing is preferably accomplished in random sites across the surface of the sanitary appliance, e.g. by embossing.

12 Claims, 7 Drawing Figures

U.S. Patent  Feb. 16, 1982  Sheet 1 of 3  4,315,507 the invention relates to a sanitary appliance, e.g. a
SANITARY NAPKIN WITH HEAT FUSIBLE BAFFLE

FIELD OF THE INVENTION

This invention relates to a sanitary appliance, e.g. a sanitary napkin and particularly to sanitary appliances including fluid pervious baffles.

BACKGROUND OF THE INVENTION

Sanitary napkins and other sanitary appliances generally contain an absorbent medium to retain body exudates and secretions and a fluid impervious liner to prevent flow of fluid through the absorbent material. In some instances, sanitary appliances also include an upper fluid pervious layer to protect the source of fluid flow, e.g. a wound surface or body opening from direct contact with the absorbent material. The inclusion of such a layer is desirable to prevent the sloughing off of absorbent material into the surface of the wound or into a body orifice.

Sanitary napkins have, in the past, been made with a variety of constructions in which the fluid impervious baffle is always attached to the absorbent material by adhesive means. For example, sanitary napkins now being sold under the NEW FREEDOM trademark by Kimberly-Clark Corporation feature a fluid impervious wrap which completely surrounds an absorbent matrix. The overlapped wrap is sealed by means of adhesive strips which penetrate the overlap layer. Between the absorbent matrix and the fluid pervious wrap is a fluid impervious baffle which is adhered to the wrap by traditional adhesive means.

Another type of construction known in the sanitary napkin art is generally described in U.S. Pat. No. 4,079,739, issued to Howard A. Whitehead and assigned to Kimberly-Clark Corporation. This particular patent describes a die cut pad which features coterminous layers of absorbents and a baffle and, in one embodiment, an outer fluid permeable wrap. In this particular patent, integrity of the absorbent layer is obtained by compressing a distinct spaced pattern along its surface. This pad integrity is obviously important in instances where no fluid pervious wrap is utilized. The baffle is adhesively attached to the absorbent portion. Other pads have been developed in which the fluid impervious baffle overlaps the side and, in some instances, portions of the top of the absorbent material but because it is desirable to maintain the baffle position relative to the position of the absorbent matrix, it has been necessary to adhesively adhere the baffle to the absorbent matrix at least in some portion of the area in which they are in juxtaposition.

There are several disadvantages inherent in the inclusion of adhesive both from the product standpoint and from the standpoint of the manufacturing operation itself. First, with regard to the product, the inclusion of adhesive adds undesirable rigidity and loss of perceived softness to the sanitary napkin or, any other sanitary appliance for that matter. From the manufacturing standpoint, an additional step is needed to apply the adhesive which complicates and slows the manufacturing process and, also, adds an additional cost factor by its existence.

SUMMARY OF THE INVENTION

According to this invention, the problems inherent in adhesively attaching the baffle to the absorbent matrix in a sanitary appliance are eliminated by utilizing a baffle having at least a two layer system with at least one of the layers making up the baffle being heat fusible.

According to this invention, a baffle is composed of at least two layers of distinctly different materials. One of these layers is a thermoplastic material with fusion temperature significantly lower than the other layer. For purposes of this invention, the fusible component must be fusible with the absorbent matrix at temperatures below approximately 180° C., i.e. the heat degradation temperature of cellulose. While cellulose tends to degrade between 150° and 200° C., there is some substantial loss of absorbency encountered at about 180° C. and since cellulosic components are commonly used as at least part of the absorptive layer in sanitary appliances, particularly sanitary napkins and diapers, the 180° C. limitation is a practical one. Obviously, in the case of absorbents which do not contain cellulose or cellulose derived materials then fusible is subject to a redefinition based upon undesirable thermal degradation of these products. Typically, such a baffle would be made by coextruding to thermoplastic materials. Such films are currently available under the tradename CROWN ZEELON by Crown Zellerbach Corporation. Examples of such composite films can be found in U.S. Pat. No. 3,843,478 assigned to Crown Zellerbach Corporation. In the particular patent, an ethylenepropylene block copolymer is coextruded with a low density polyethylene. Other coextruded films containing at least two layers of thermoplastic materials with significantly different melting temperatures are similarly suitable.

While coextrusion is a valuable method in producing two or three layer composite sheets of polymers having different melting characteristics, as disclosed in U.S. Pat. No. 3,843,478, it is not the only method for producing such a polymeric sheet. An alternative method is to cast a high melting point polymer and then fuse a lower melting point polymer in sheet form to the surface or surfaces of the higher melting point polymer. This method of producing polymeric composites is well known and need not be elaborated on here.

With regard to the fusing itself, the fusing bond will be substantially increased if the absorbent layer contains at least some additional fusible material. That material may be directed toward the portion of the layer which contacts the fusible surface of the baffle or can be randomly dispersed throughout the absorbent matrix. When fusible material is present in the absorbent matrix, the maximum temperature depends upon that which is necessary to produce some degree of fusion between the fusible material and the absorbent matrix and the fusible baffle component. This temperature may be substantially less than 180° C. In fact, where a fusible material is present, the fusion temperature may be substantially below the 180° C. figure and may be as low as 90° C.

Examples of suitable fusible materials are ethylene vinyl acetate copolymers such as those having a vinyl acetate content of 3 to 28 percent and a melting point range of 90° to 110° C.; ethylene methyl acrylate copolymer having a melting point range between 90° and 110° C.; ethylene acrylic acid copolymers having a melting point range between 80° and 110° C. and low density polyethylene having a melting point range between 110° and 130° C. Higher melting point polymers which can be used as the nonfusible component of the baffle when mated with the films described above may include, for example, high density polyethylene with a melting point range of 130° to 140° C.; polypropylene having a melting point range of 135° to 150° C.; polybutylene with a melting point range of 125° to 135° C.; various nylons having melting point ranges between 210° and 240° C.; polyesters with melting point ranges between 150° and 180° C.; polyurethanes with melting point ranges between 150° and 180° C. and polycarbonates with melting points between 190° and 210° C. It is apparent that once the choice of the fusible component is made, a suitable component with higher melt temperature can be designated based upon the melting point of the fusible component.

Where a thermoplastic fusible material is present as a portion of the absorbent, fusing of the absorbent to the baffle is readily achieved, e.g. by the utilization of hot embossing rolls. The localized points of contact in some form of random distribution along the area and throughout the depth of the pad provides sufficient adhesion for attachment of the pad to the thermoplastic baffle. Embossment patterns can generally be of any particular configuration and may be designed to be flow directing if such is desired. It should be noted that the concept of intermingling fusible fibers with cellulosic fibers is well known in the art. One particular variation is described in U.S. Pat. No. 4,100,324 to Anderson et al and relates to a mixture of meltblown thermoplastic fibers and conventional cellulosic fibers laid down as an integral mat. Embossing of an integral combination of fusible and nonfusible fibers will produce localized absorbency retardant or fluid impermeable sites. As a result, it is preferred that these areas be randomly spaced and occupy no more than about 10 to 15 percent of the surface area of the napkin.

An especially desirable variation on the concept of this invention is the utilization of a three component sheet, the outer component of which would be a roughened finish discussed above and would provide a roughened frictional surface so that the conventional adhesive attachment for napkins to panties could be avoided. The type of finish produced could in fact be produced on the nonfusible portion of the sheet but it would be substantially more difficult to do so. The process of the invention, in its simplest embodiment, merely involves the fusing of the absorbent material having a fusible component to a fusible layer of the baffle. Variations on this process depend upon the particular design of the sanitary napkin desired, i.e. two fusible surfaces can be provided on the baffle with a napkin having a fusible body contact layer serving as an overwrap. In this case, the absorbent material is fused to a fusible surface of the fluid impervious baffle and the overwrap is fused to the second fusible surface of the baffle. This can be done in a single step after the baffle is placed on the absorbent material and the overwrap is laid over the baffle portion. As mentioned in conjunction with the description of the sanitary napkin, embossment is a preferred method of providing the necessary fused attachment. Fusing temperatures, as mentioned previously, are dependent upon both the nature of the fusible surface of the baffle, the fusible component of the absorptive material and, if utilized, a fusible overwrap.

Examples of specific embodiments of the napkin of this invention follow in the drawings described below. These examples, as indicated from the preceding description, are merely illustrative of some of the possible embodiments utilizing the broad concept of this invention and while they are presently preferred are by no means exhaustive.

DESCRIPTION OF THE DRAWINGS

Examples of preferred embodiments of this invention can more readily be understood by the drawings described below in which:

FIGS. 1, 3, 4, 5, and 6 are lateral cross sections of different embodiments of this invention while

As can be seen in FIG. 1, an absorbent matrix 10 is completely encircled by a body contact layer 14 which is fluid pervious. At the bottom of the napkin is baffle 11 comprised of a fusible layer 11a and a nonfusible layer 11b. An adhesive strip 12 is utilized to seal the edge of the body contact layer 14 at its overlap as well as to provide an adhesive surface for attachment to the panty after release layer 13 is peeled away. FIG. 2 depicts a typical wrapped napkin configuration representative of this broad class of sanitary napkins.

FIG. 3 is identical to FIG. 1 in all respects except layers 11a and 11b are reversed and, in this instance, the wrap 14 which is fusible is fused to the fusible baffle layer 11a. This particular embodiment is especially preferred where there is no fusible material spaced in the absorbent. Another, modified wrapped napkin is depicted in FIG. 5. In this particular figure, the fluid pervious fusible wrap completely encircles the absorbent material only and it is fused to fusible surface 11a of the baffle which is external to the other components of the pad. In FIG. 5, a third layer 11c is depicted which provides a roughened frictional surface for attachment of the napkin to the feminine undergarment. The absorbent matrix 10 in FIG. 5 may contain fusible fibers but, as is the case with the embodiment depicted in FIG. 3, fusing can occur without the presence of such fibers. If embossing is desired, however, in contradistinction to a substantially greater application of heat and overall fusing, the presence of fusible fibers throughout the matrix is believed to be required.

FIGS. 4 and 6 are examples of the sandwich construction found in some feminine napkins. The difference between these two figures is the presence, in FIG. 6, of a roughened third layer 11c for panty attachment while in FIG. 4 modified cast nonfusible layer 11d provides the same function. As can be seen in FIG. 4, the absorbent material 10a contains fusible filaments 10b. In this particular configuration, the absorbent is fused directly to the fusible baffle. This absorbent fusing can occur in any of the other configurations in which a fusible layer of the baffle is adjacent to the fusible absorbent and/or a fusible wrap is interposed between a fusible absorbent and a fusible baffle.

Figure 1:
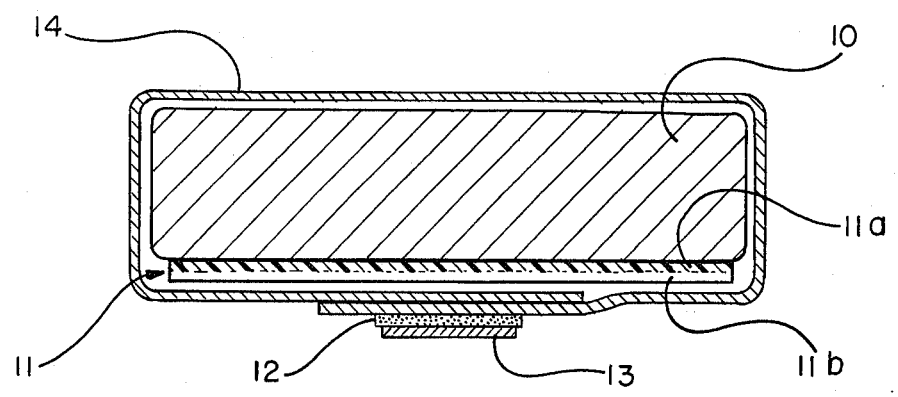
Figure 2:
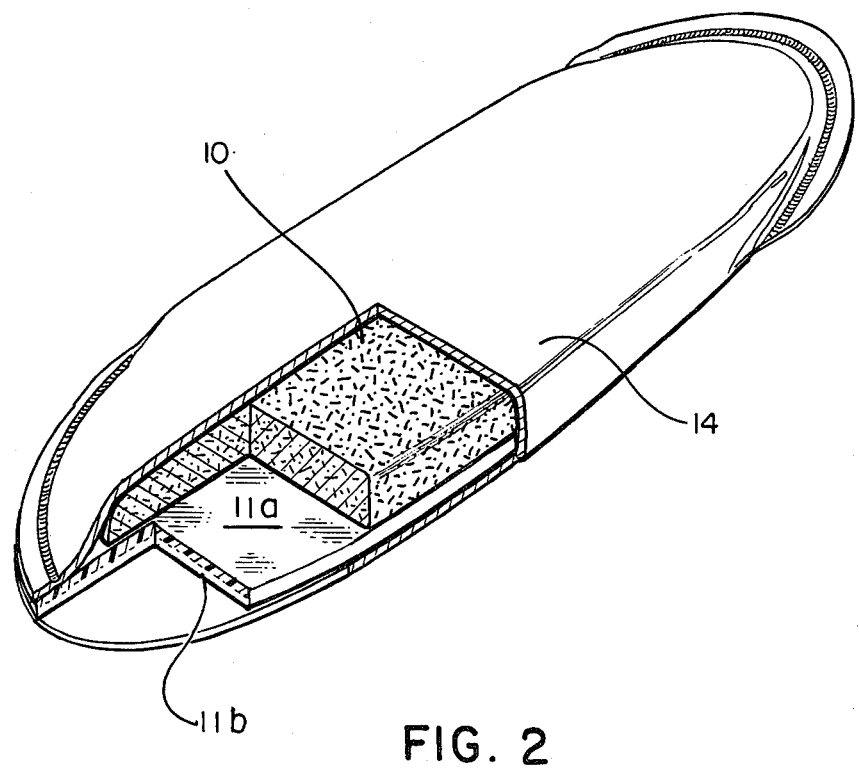
FIG. 2 is a side perspective view of a wrapped napkin according to the teachings of this invention and FIG. 7 is a plan view partially in cross section of another embodiment of the concept of this invention.
Figure 3:
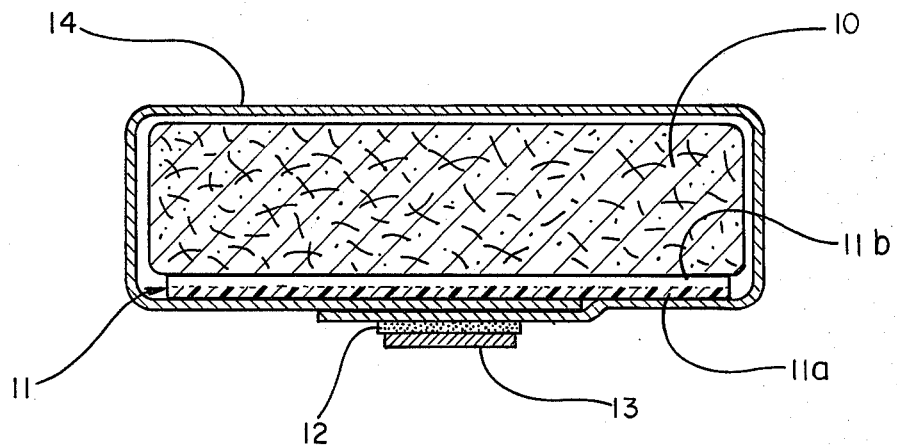
Figure 4:
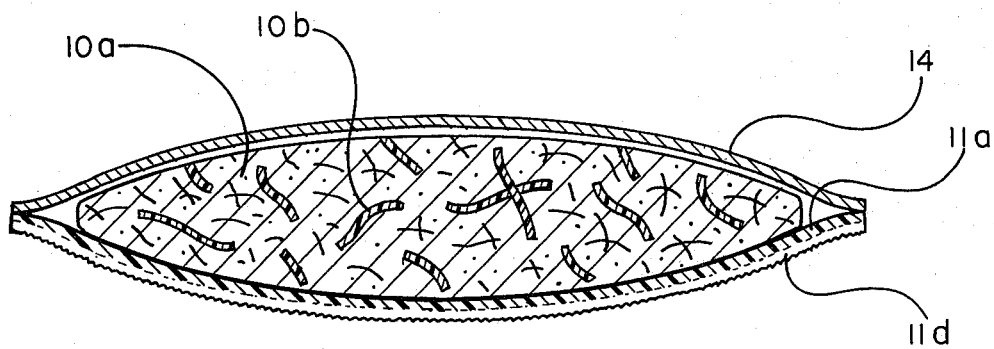
Figure 6:
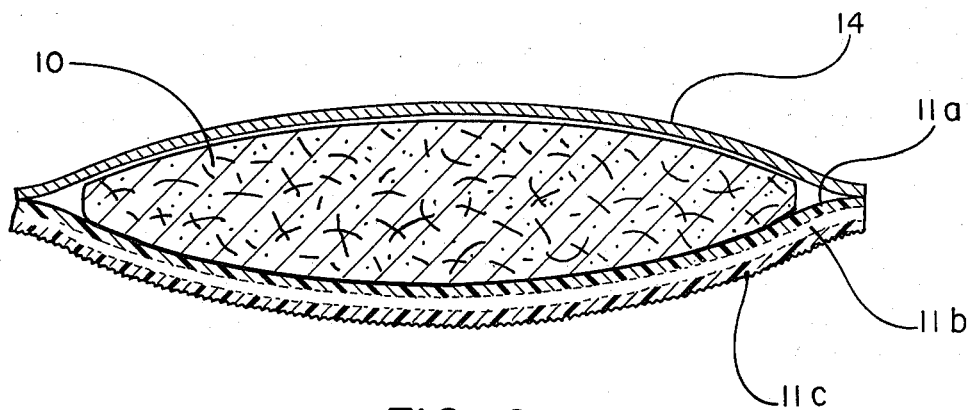
Figure 5:
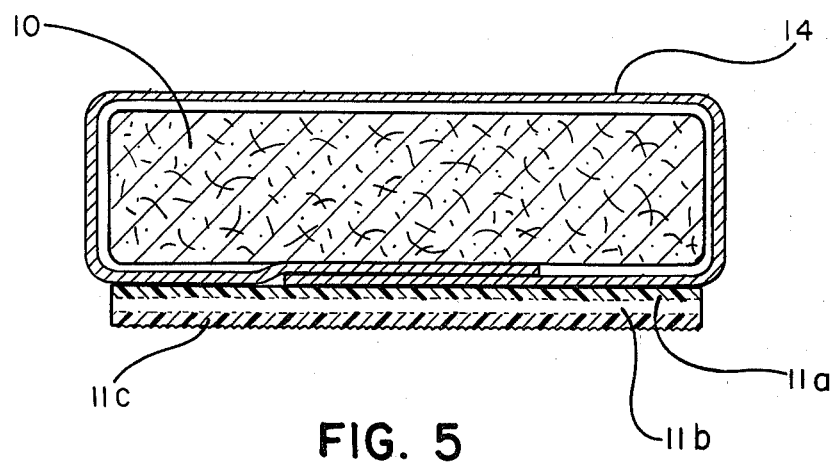
Figure 7:
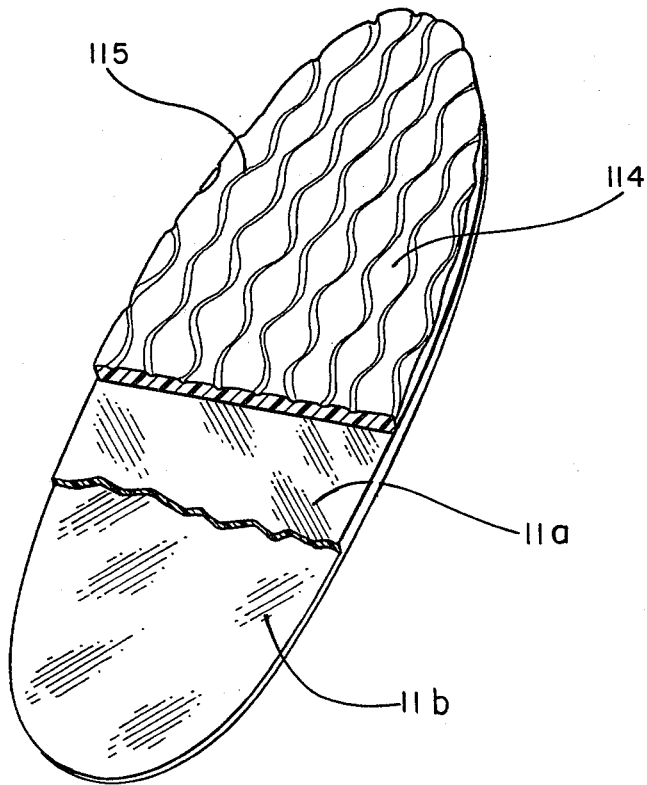

It is, of course, possible and even desirable to fuse the embodiments depicted at FIGS. 4 and 6 as is shown for example in FIG. 7. The embodiment in FIG. 7 differs from those previously in that the cover material 114 is also absorbent and therefore if a panty shield type of product or a so-called mini pad is desired, additional absorbent material may not be needed. U.S. Pat. No. 4,100,324 mentioned previously provides a material which can be rendered suitably absorbent for this purpose with the proper choice of cellulosic material to meltblown polymer ratios. If is, of course, possible and may even be desirable in certain circumstances to provide a separate absorptive layer and this is contemplated within the scope of the invention. If such a layer is provided, however, it is preferred that it contain at least some fusible material. It should be noted that the embossed lines 115 are three dimensional and do in fact provide the localized fusing discussed previously.

What is claimed is:

1. A multilayer sanitary appliance comprising a fluid pervious body contact layer, an absorbent layer and a fluid impervious exposed thermoplastic baffle, said baffle having at least two adjacent layers of material a first of which is fusible with at least a first of said layers being fused to either the body contact layer or the absorbent layer and another of said layers being nonfusible at temperatures greater than at least said first of said baffle layers.

2. A diaper comprising a fluid pervious body contact layer, an absorbent layer and a fluid impervious exposed thermoplastic baffle having at least two adjacent layers of material a first of which is fusible with at least a first of said layers being fused to either the body contact layer or the absorbent layer and another of said layers being nonfusible at temperatures greater than at least said first of said baffle layers.

3. A sanitary napkin comprising a fluid pervious body contact layer, an absorbent layer and a fluid impervious exposed thermoplastic baffle positioned adjacent the wearer's undergarment, said baffle having at least two adjacent layers with at least a first of said layers being fused to either the body contact layer or the absorbent layer and another of said layers being nonfusible at temperatures greater than at least said first of said baffle layers.

4. A sanitary napkin according to claim 3 wherein one of said layers is fused to the absorbent layer.

5. A sanitary napkin according to claim 3 or 4 wherein said absorbent layer includes a fusible thermoplastic.

6. A sanitary napkin according to claim 3 or 4 wherein the baffle is fused to the fluid pervious body contact layer.

7. The sanitary napkin according to claim 3 wherein the baffle has at least one adhesive strip and a release liner attached thereto for undergarment attachment.

8. The sanitary napkin according to claims 1 or 3 in which the baffle has a third undergarment contact layer which has a frictional surface for undergarment contact.

9. The sanitary napkin according to claims 1 or 3 wherein the body contact layer is absorbent.

10. The sanitary napkin according to claims 1 or 3 wherein the absorbent contains fusible material interspersed therein.

11. A sanitary napkin comprising an absorbent layer with fusible material interspersed therein and a baffle having at least two adjacent layers, one of said layers being fusible at temperatures not greater than that needed to fuse the fusible material in the absorbent.

12. The sanitary napkin according to claims 1, 3, 4 or 11 wherein at least the absorbent portion of the sanitary napkin has an embossed pattern.

* * * * *